US00PP25861P3

(12) United States Plant Patent
Leis et al.

(10) Patent No.: US PP25,861 P3
(45) Date of Patent: Sep. 8, 2015

(54) APPLE TREE NAMED 'SINFONIA'

(50) Latin Name: ***Malus domestica* Mill.**
Varietal Denomination: Sinfonia

(71) Applicant: C.I.V.—CONSORZIO ITALIANO VIVAISTI—SOCIETÀ CONSORTILE A R.L., Comacchio FE (IT)

(72) Inventors: Michelangelo Leis, Ferrara (IT); Alessio Martinelli, Ferrara (IT); Francesco Tagliani, Argenta (IT); Gianfranco Castagnoli, Quingentole (IT)

(73) Assignee: C.I.V.—CONSORZIO ITALIANO VIVAISTI—SOCIETA CONSORTILE A R.L., Comacchio FE (IT)

( * ) Notice: Subject to any disclaimer, the term of this patent is extended or adjusted under 35 U.S.C. 154(b) by 193 days.

(21) Appl. No.: 13/986,176

(22) Filed: Apr. 9, 2013

(65) Prior Publication Data

US 2014/0165239 P1 Jun. 12, 2014

(30) Foreign Application Priority Data

Dec. 11, 2012 (QZ) ..... PBR 2012/2804

(51) Int. Cl.
*A01H 5/08* (2006.01)

(52) U.S. Cl.
USPC ..... Plt./161
CPC ..... *A01H 5/0875* (2013.01)

(58) Field of Classification Search
USPC ..... Plt./161, 172
CPC ..... A01H 5/0875; A01H 5/08
See application file for complete search history.

*Primary Examiner* — Kent L Bell
(74) *Attorney, Agent, or Firm* — Foley & Lardner LLP

(57) ABSTRACT

A new and distinct *Malus domestica* Mill. apple tree named 'Sinfonia' particularly characterized by having a mid-season ripening time, with high productivity and precocious fruit bearing. The fruit are of big size, with conic shape. The overcolor is light red over green background. The flesh is very firm with fine texture and good juiciness. The flavor is slightly acidic with a global excellent eating quality. The fruit keeps very well on the tree, as well as in cold storage.

4 Drawing Sheets

Latin name of the genus and species of the plant claimed: *Malus domestica* Mill.

Variety denomination: 'Sinfonia'.

PRIORITY CLAIM

This application claims priority to European Community Plant Variety office application No. 2012/2804 filed Dec. 11, 2012, the disclosure of which is incorporated by reference herein in its entirety.

BACKGROUND OF THE INVENTION

The present invention relates to a new and distinct variety of apple tree, botanically known as *Malus domestica* Mill. of the Family Rosaceae, and hereinafter referred to by the variety denomination 'Sinfonia'.

The new *Malus* variety is a product of a planned breeding program conducted by the inventors, Michelangelo Leis, Alessio Martinelli, Francesco Tagliani and Gianfranco Castagnoli in S. Giuseppe di Comacchio (Ferrara), Italy. The objective of the breeding program was to develop new *Malus* varieties with improved production characteristics, high-quality flavour and aroma and sustainability by increasing the tree's natural resistance. The primary objective of the research program is to selection new apple varieties with natural resistances, in particular to scab.

The new *Malus* variety 'Sinfonia', originated from a cross made in a planned, controlled breeding program in S. Giuseppe di Comacchio (Ferrara), Italy. The female parent is the apple tree variety 'Co-op 25' (patented; U.S. Plant Pat. No. 12,323). The male parent is an unpatented, proprietary selection denominated 'CIVCP-142'. 'Sinfonia' was discovered and selected in October 2000 by the inventors as a flowering plant within the progeny of the stated cross in a controlled environment in S. Giuseppe di Comacchio (Ferrara), Italy.

Asexual reproduction of the new *Malus* variety by budding and grafting was first performed in August 2001 and in the following years in S. Giuseppe di Comacchio (Ferrara), Italy, and has demonstrated that the combination of characteristics as herein disclosed for the new *Malus* variety are firmly fixed and retained through successive generations of asexual reproduction. The new variety reproduces true to type.

BRIEF DESCRIPTION OF THE INVENTION

The following traits have been repeatedly observed and are determined to be unique characteristics of 'Sinfonia' which in combination distinguish this apple tree as a new and distinct variety:

1. Bi-colored variety with intense light red overcolor;
2. Big size;
3. Weak vigor, open habit with short branches;
4. High sugar content and
5. Long storage ability.

When compared to plants of the parent varieties, the claimed variety 'Sinfonia' differs primarily in the traits listed in Table 1 below:

TABLE 1

| Comparison with parent varieties | | | |
|---|---|---|---|
| Characteristic in which the variety is different | State of expression of candidate variety | The female parent (Co-op 25) | The male parent (CIVCP-142) |
| Resistance to scab | Not | Yes | Not |
| Fruit: over color | Orange red | Red | Light red |
| Fruit: relative area of over color | Medium | Medium | Small to medium |
| Time of eating maturity | Medium to late | Medium | Late to very late |

When compared to plants of the related variety 'Majesty' (U.S. Plant patent application Ser. No. 13/986,175), the claimed variety differs primarily in the traits listed in Table 2 below:

TABLE 2

| Comparison with related variety | | | |
|---|---|---|---|
| Denomination of sibling cultivar | Characteristic in which the sibling cultivar different | State of expression of sibling cultivar | State of expression of candidate variety |
| 'Majesty' | Time of eating maturity | Late | Medium to late (twenty days before 'Majesty') |
| | Fruit: overcolor | Purple red | Orange red |
| | Fruit: size | Large | Very large |

Of the commercial cultivars known to the inventors, the most similar in comparison to the new apple tree variety 'Sinfonia' is the variety 'Galaxy' (unpatented). In comparison to the similar variety 'Galaxy', 'Sinfonia' differs primarily in the traits listed in Table 3 below.

TABLE 3

| Comparison with Similar Variety | | | |
|---|---|---|---|
| Denomination of similar variety | Characteristic in which the similar variety is different | State of expression of similar variety | State of expression of candidate variety |
| 'Galaxy' | Hue of over color | Red | Orange red |
| | Pattern of over color | Solid flush with weakly defined stripes | Only solid flush |
| | Time of eating Maturity | Medium | Medium to late |

BRIEF DESCRIPTION OF THE DRAWINGS

The accompanying photographs illustrate the overall appearance of the new apple tree 'Sinfonia' showing the colors as true as is reasonably possible with color reproductions of this type. Color in the photographs may differ slightly from the color value cited in the detailed botanical description, which accurately describe the color of 'Sinfonia'. In some of the photographs a label shows the breeder's reference for 'Sinfonia', 'YX-2'.

DETAILED BOTANICAL DESCRIPTION

Figure 1:
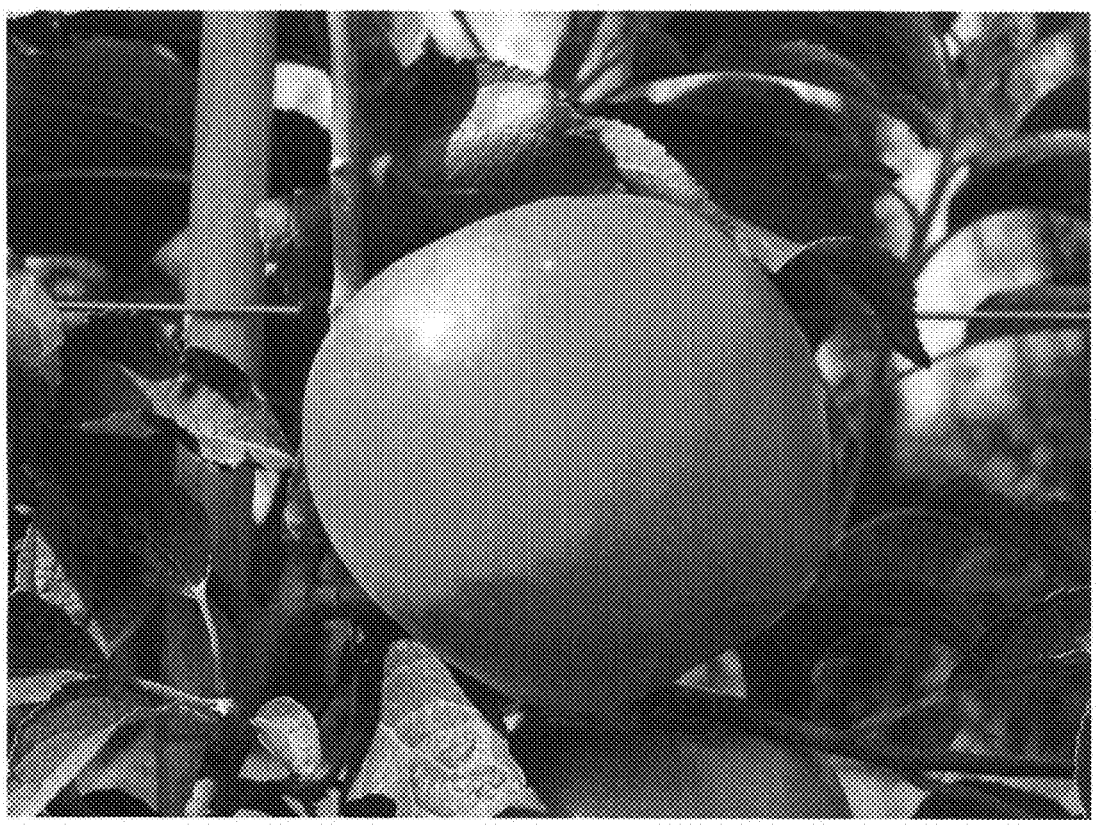
FIG. 1: illustrates a close-up view of typical fruit, branches, and leaves of 'Sinfonia'.
Figure 2:
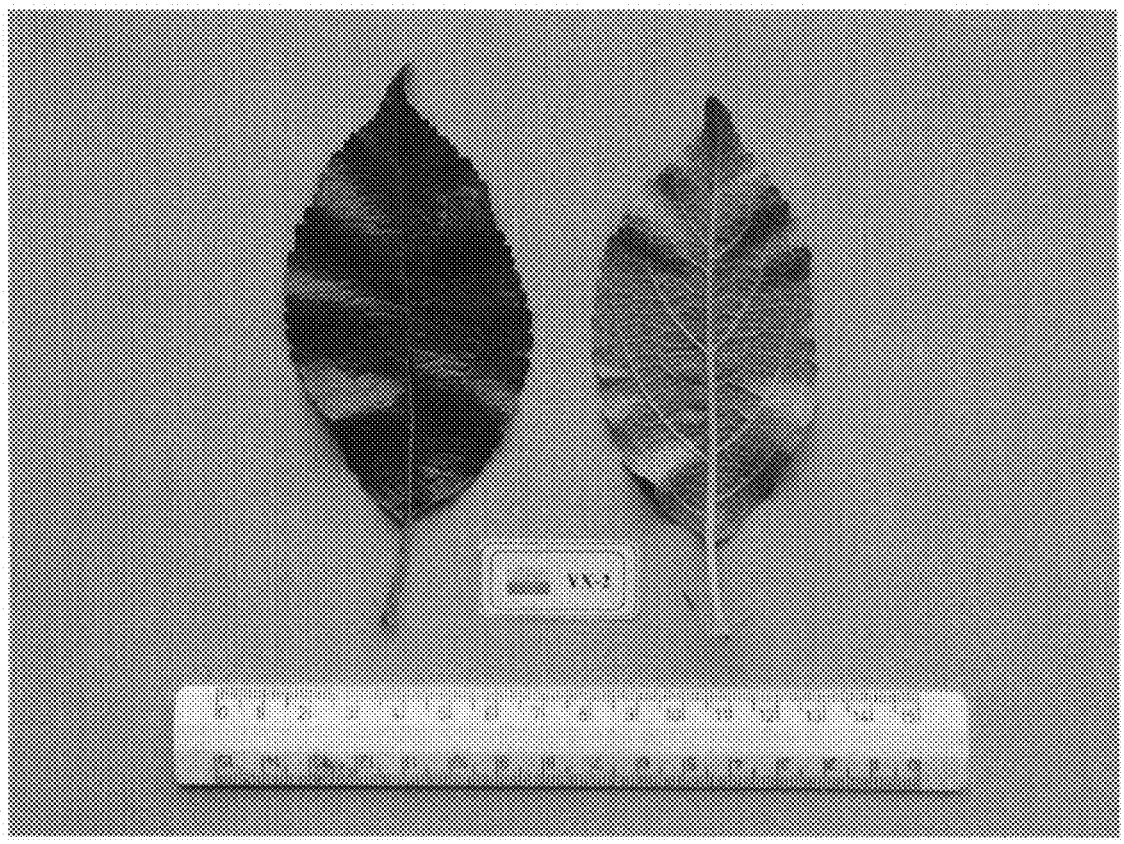
FIG. 2: illustrates the leaves of 'Sinfonia'.
Figure 3:
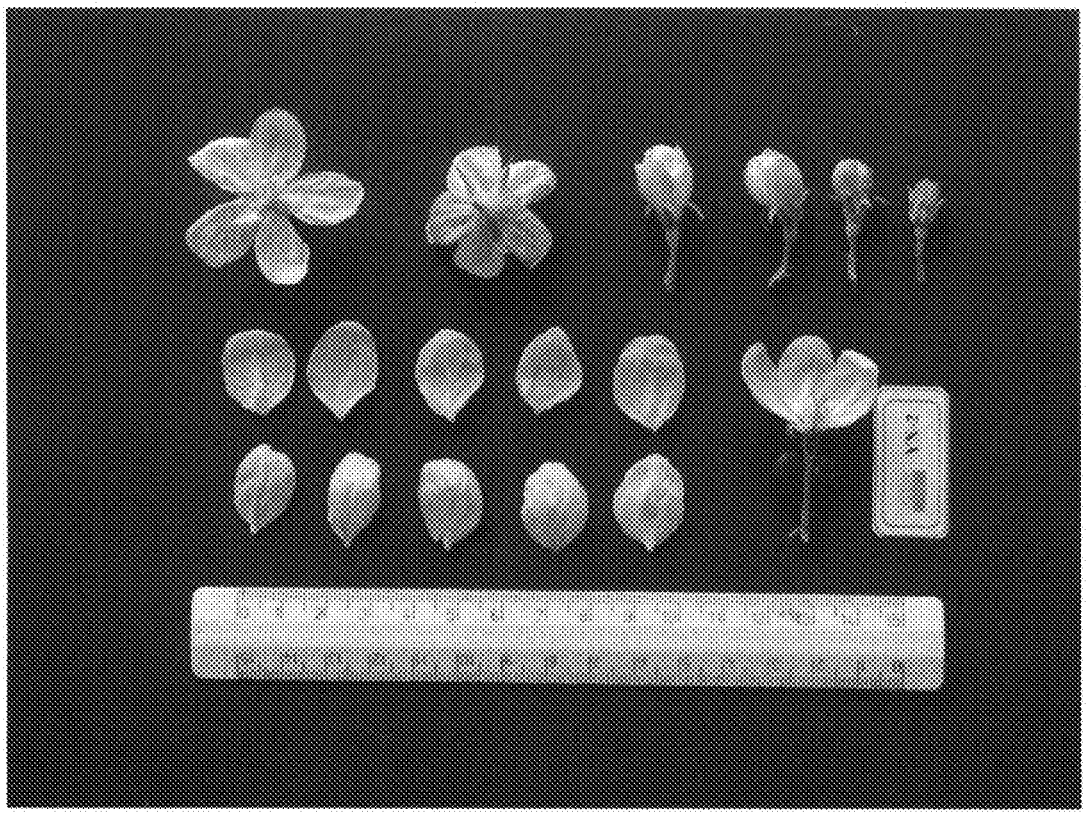
FIG. 3: illustrates the flowers of 'Sinfonia'.
Figure 4:
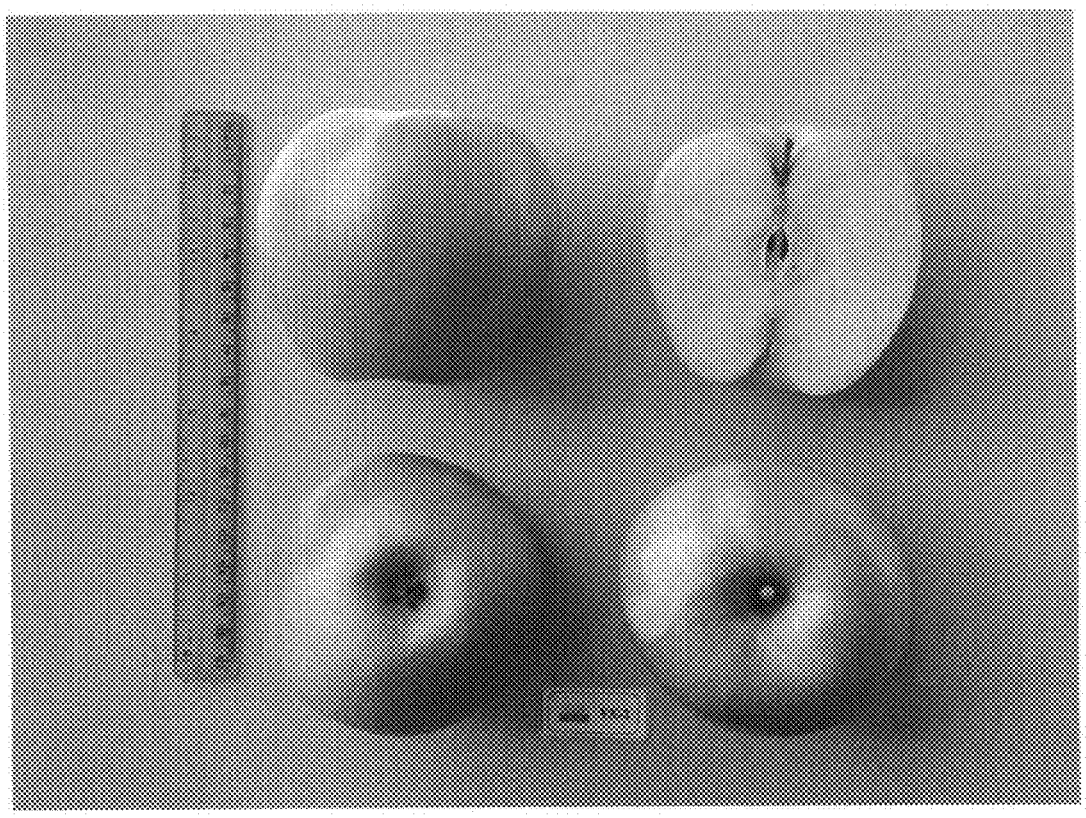
FIG. 4: illustrates the fruits of 'Sinfonia'.

The new *Malus* variety 'Sinfonia' has not been observed under all possible environmental conditions. The phenotype of the new variety may vary with variations in environment such as temperature, light intensity, and day length without any change in the genotype of the plant.

The aforementioned photographs, together with the following observations, measurements and values describe the new *Malus* variety 'Sinfonia' as grown in the apple farm in S. Giuseppe di Comacchio (Ferrara), Italy, under conditions which closely approximate those generally used in commercial practice. The apple farm where 'Sinfonia' is grown is situated near the Adriatic sea (44°45' North, 12° 11' East) and is zero (0) meters above sea level. The soil of the apple farm where 'Sinfonia' is grown is sandy, and the soil is treated with manure every year and irrigated with drip irrigation systems. The climate is temperate continental with high summer temperatures and low winter temperatures.

Unless otherwise stated, the detailed botanical description includes observations, measurements and values based on four (4) year old 'Sinfonia' trees that were grown in the apple farm in S. Giuseppe di Comacchio (Ferrara), Italy, from 2008 to 2011 All trees were of cropping maturity. Quantified measurements are expressed as an average of measurements taken from a number of individual trees of 'Sinfonia'. The measurements of any individual tree, or any group of trees, of the new variety may vary from the stated average.

Color references are made to The Royal Horticultural Society Colour Chart (R.H.S.), except where general colors of ordinary significance are used. Color values were taken under daylight conditions at approximately at 10:00 am in S. Giuseppe di Comacchio (Ferrara), Italy.

All trees of 'Sinfonia', insofar as they have been observed, have been identical in all the characteristics described below.

Classification:

*Botanical.*—*Malus domestica* Mill.

Parentage:

*Female parent.*—*Malus domestica* Mill. 'Co-op 25' (patented; U.S. Plant Pat. No. 12,323).

*Male parent.*—*Malus domestica* Mill. 'CIVCP-142' (unpatented, proprietary selection).

Propagation: Budding and grafting on M9 rootstock.

Tree:

*Age.*—Observed plants were four years old.

*Vigor.*—Weak.

*Tree type.*—Ramified.

*Habit.*—Spreading, branches angle is typically 45° to 55° degrees from the vertical stem.

*Density.*—Medium density.

*Cropping behavior.*—Precocious fruit bearing with high productivity.

*Type of bearing.*—Typically long shoot, presence of spur on 2-3 year old shoots.

*Production.*—$4^{th}$ year: about 15 Kg.

*Size.*—Height: 2.40 m. Spread: 1.10 m. Trunk Diameter: about 35 mm as measured 20 cm above point of grafting.

*Surface texture*.—Smooth.

*Bark color*.—Greyed RHS 197 A.

*Trunk lenticels*.—

*Overall shape*.—Round to elongated. Length: average 2.0 mm. Width: average 1.0 mm. Color: greyed-orange RHS 163 B. Density: about 2 to 3 per $cm^2$.

*Branches*.—Number per tree: about 30 at four (4) years. Length: Varies due to pyramidal shape of tree. At four (4) years, maximum of 60 cm to 80 cm; minimum of 30 cm to 50 cm. Diameter (at 3 years): About 10 mm to 14 mm in middle. Surface texture: smooth. Color (at 3 years): grey RHS 199 A. Internode length: About 2.5 cm to 4.0 cm. Internode diameter: About 10 mm to 14 mm.

*Branches lenticels*.—Length: about 1.2 mm. Width: about 0.8 mm. Color: greyed-orange RHS 164 C. Density: About 2 per $cm^2$.

Leaves:

*Arrangement*.—Alternate, simple, petiolated.

*Lamina*.—Size: Length (4 year old): average 94.8 mm (from $3^{rd}$ to $5^{th}$ fully expanded leaf). Width (4 year old): average 48.1 mm (from $3^{rd}$ to $5^{th}$ fully expanded leaf). Length/width ratio: 1.97. Overall Shape: narrow-elliptic. Base shape: narrow. Apex shape: pointed. Margin: bicrenate. Pubescence: absent on upper surface and weak pubescent on lower surface. Attitude in relation to shoot: outwards. Color (mature leaves): green RHS 139 A on the upper side and 138 B underside. Color (immature leaves): green RHS 144 A on the upper side and 146 C underside.

*Venation*.—Type: prominent pinnate venation from a midrib to the edge. Color: yellow-green RHS 145 C.

*Petiole*.—Length: about 23 mm. Diameter: about 1.9 mm. Texture: hairy. Color: yellow-green, RHS 138 B with anthocyanin coloration located on the base, RHS 64 B red-purple group.

*Stipule*.—Arrangement: adnate, grown together; small size. Length: average 7.5 mm. Width: average 0.8 mm. Distance of stipules from basal attachment of petiole: average 3.0 mm.

Spur:

*Present*.—On 2-3 year old shoots.

*Distance between each spur*.—On the two-three year old branches, the distance is about 20 mm to 35 mm.

*Number of fruit per spur*.—4 to 5 without thinning.

Flowers:

*Blooming time*.—Full bloom on Apr. $6^{th}$ in S. Giuseppe di Comacchio (Ferrara) in year 2012.

*Blooming period*.—9 to 13 days.

*Fragrance*.—Slight.

*Type*.—Corymb.

*Number of flowers per corymb*.—5.

*Flower size*.—Diameter: about 40 mm.

*Flower depth* (*height of the corolla*).—About 8 to 9 mm, measured when the flowers are fully open. Flower color: Primarily white RHS 155D with shades RHS 63 D when petals are fully opened, undersides of petals there are shades red-purple RHS 67 A.

*Color of unopened flower* (*balloon stage*).—Red-purple group RHS 60 D.

*Buds*.—Number of buds per spur: typically, one per spur. Shape: pointed. Length: about 8 mm. Width: about 4 mm. Color: brown, RHS 200 B with hairy surface.

*Petals*.—Arrangement: touching. Number per flower: five (5). Length: average 24.2 mm. Width: average 15.6 mm. Length/width ratio: 1.55. Overall shape: elliptic. Apex shape: rounded. Base shape: narrow. Texture: smooth. Margin: entire. Color (upper surface): white, RHS 155 D with shade red-purple RHS 63 D. Color (lower surface): white, RHS 155 D with shade red-purple RHS 67 A.

*Sepals*.—Number per flower: five (5). Length: average 10.43 mm. Width: average 3.36 mm. Length/width ratio: 3.1. Overall shape: lanceolate. Apex shape: pointed. Texture: hairy. Margin: entire. Color: green RHS 138 A upper side; green RHS 138 B lower side.

*Pedicel*.—Length: average 16.5 mm. Diameter: 2 to 3 mm. Texture: hairy. Color: green RHS 138 C.

Fruit:

*Keeping quality*.—The fruits have a long shelf life, up to two weeks without losing firmness and juiciness.

*Maturity when described*.—Ripe for eating.

*Maturity period after full bloom*.—About 142 days in S. Giuseppe di Comacchio (Ferrara) Italy.

*Date of first and last pickings*.—About 29 Aug. and 10 Sep. in S.Giuseppe di Comacchio (Ferrara) Italy (North 44°45'46.2", East 012°11'31.9") in year 2011.

*General shape*.—Conic.

*Average weight*.—263 g.

*Fruit size*.—Average height: 77.8 mm. Average diameter (at widest point): 87.0 mm.

*Position of maximum diameter*.—Between ¾ of the height near stem end and half of the fruit.

*Height/diameter ratio*.—0.89.

*Stem*.—Length: average 20.8 mm. Diameter: average 2.1 mm. Color: yellow-green, RHS 146 C.

*Stalk cavity*.—Depth: average 20.3 mm. Width: average 39.2 mm.

*Eye basin*.—

*Aperture of eye*.—Closed. Depth: average 12.3 mm. Width: average 32.4 mm. Crowning at calyx end: moderate. Position of sepals: wrapping. Calyx tube: funnel form.

*Skin*.—Thickness: medium. Texture: slightly rough. Bloom: absent or very low. Greasiness: absent or very weak. Firmness (at picking time): 8 to 9 kg/$cm^2$. Overcolor color: light red RHS 50 B. Percentage of skin surface with overcolor color: medium. Pattern of overcolor: only solid flush. Intensity of overcolor: medium. Ground color: yellow-green RHS 146 C.

*Skin lenticels*.—Length: about 0.4 mm. Width: about 0.4 mm. Color: greyed-orange RHS 165 C. Density: about 4 per $cm^2$ in the central area of the surface of fruit. The number of lenticels increases in a direction toward the hollow of the calyx.

*Flesh*.—Color: yellow RHS 11 D. Texture: fine. Tipe of flesh: crisp and juicy. Firmness: firm. Aroma: intense. Eating quality: good with high level content in sugar. Sugar content (at picking time): 14 to 14.5° Brix. Acidity/Starch (at picking time): Acidity: 7.0 to 7.5 g/l Malic acid/starch: 2.5-3.0. Laimburg scale 1 to 5.

*Core*.—Symmetry of core: slightly asymmetric. Distinctness of core lines: no more evident. Locules: Number (per fruit): 5 (five). Length: average 11.4 mm. Width: average 5.76 mm. Form: moderately open.

Seeds:

*Number per fruit*.—3 to 5.

*Number per locule*.—About 1.

*Shape*.—Elliptic. Length: average 8.3 mm. Width: average 5.3 mm.

*Color*.—Greyed-orange RHS 166 A.

Reproductive organs:

*Androecium*.—Stamens: Number per flower: about 20 (Twenty). Length: average 9.35 mm. Filament: Length: about 7.65 mm. Anther: Shape: ovoid, flat in the center. Length: 2.05 mm. Diameter: 1.63 mm. Color: yellow group RHS 12 C. Pollen: Amount: abundant. Color: yellow, RHS 13 C. Requirements: the crab apple *Malus* 'Evereste' is good pollinator.

*Gynoecium*.—Stigma: Shape: funnel shape with receptive surface on top. Length: 1.2 mm. Width: 0.75 mm. Color: yellow green group RHS 151 B. Style: Number per flower: 5 (Five). Length: about 11.3 mm. Width: about 0.35 mm. Color: yellow-green, RHS 144 D. Ovary: Length: about 3.0 mm. Width: about 2.0 mm. Color: yellow-green, RHS 144 D.

*Use*.—Fresh market.

*Sensitivity to disease/pests*.—No particular sensibilities detected.

*Winter hardiness*.—Tolerance to temperatures of −12° C. without observed damage to wood and buds of dormant apple trees; but open flowers and young fruitlets are killed by exposure to −3° C. to −5° C., depending on the length of exposure.

*Drought/heat tolerance*.—Good tolerance to heat, up to 40° C., growth is limited by drought periods without irrigation.

*Shipping/storage characteristics*.—Very good storability under ULO-conditions (1° C., 2% $0_2$, 2% $CO_2$) for up to six (6) months.

We claim:

1. A new and distinct *Malus domestica* Mill. apple tree named 'Sinfonia', substantially as illustrated and described herein.

* * * * *